United States Patent
Zhao et al.

(10) Patent No.: US 12,027,255 B2
(45) Date of Patent: Jul. 2, 2024

(54) SYSTEM FOR PREDICTING MICROSATELLITE INSTABILITY AND CONSTRUCTION METHOD THEREOF, TERMINAL DEVICE AND MEDIUM

(71) Applicant: CANCER HOSPITAL, CHINESE ACADEMY OF MEDICAL SCIENCES, Beijing (CN)

(72) Inventors: Qing Zhao, Beijing (CN); Hongxia Zhong, Beijing (CN); Hongmei Zhang, Beijing (CN); Xinming Zhao, Beijing (CN)

(73) Assignee: CANCER HOSPITAL, CHINESE ACADEMY OF MEDICAL SCIENCES, Beijing (CN)

( * ) Notice: Subject to any disclaimer, the term of this patent is extended or adjusted under 35 U.S.C. 154(b) by 0 days.

(21) Appl. No.: 18/385,401

(22) Filed: Oct. 31, 2023

(65) Prior Publication Data
US 2024/0062881 A1    Feb. 22, 2024

Related U.S. Application Data

(63) Continuation of application No. PCT/CN2022/114898, filed on Aug. 25, 2022.

(30) Foreign Application Priority Data

May 25, 2022    (CN) .......................... 202210574938.9

(51) Int. Cl.
*G16H 30/00*    (2018.01)
*G16H 30/40*    (2018.01)
*G16H 50/30*    (2018.01)

(52) U.S. Cl.
CPC ............. *G16H 30/40* (2018.01); *G16H 50/30* (2018.01)

(58) Field of Classification Search
CPC ............................... G16H 30/40; G16H 50/30
See application file for complete search history.

(56) References Cited

U.S. PATENT DOCUMENTS

| | | | |
|---|---|---|---|
| 2008/0096197 A1* | 4/2008 | Findeisen | C12Q 1/6886 435/6.12 |
| 2009/0274681 A1* | 11/2009 | Bellacosa | A61P 43/00 204/461 |

(Continued)

FOREIGN PATENT DOCUMENTS

| | | |
|---|---|---|
| CN | 110265095 A | 9/2019 |
| CN | 111028223 A | 4/2020 |

(Continued)

*Primary Examiner* — Khai M Nguyen
(74) *Attorney, Agent, or Firm* — Bayramoglu Law Offices LLC

(57) ABSTRACT

A system for predicting microsatellite instability and a construction method thereof, a terminal device and a medium are provided. Target image information, pathological specimen information and clinical data information of a user to be predicted are acquired by an acquisition module in the system for predicting microsatellite instability; a radiomics signature is generated according to the target image information, and a pathomics signature is generated according to the pathological specimen information, by a signature generation module, based on a pre-trained MSI-H/dMMR multi-omics signature model; and MSI-H/dMMR prediction results are generated according to the radiomics signature, the pathomics signature and the clinical data information, by a prediction generation module, based on a pre-trained MSI-H/dMMR prediction model.

7 Claims, 6 Drawing Sheets

(56) References Cited

U.S. PATENT DOCUMENTS

| | | | | |
|---|---|---|---|---|
| 2020/0024669 A1* | 1/2020 | Spetzler | ............... | G16H 10/40 |
| 2021/0090694 A1* | 3/2021 | Colley | ................ | G16H 15/00 |
| 2021/0198748 A1* | 7/2021 | Danaher | ............ | C12Q 1/6886 |
| 2023/0230661 A1* | 7/2023 | Yeh | .................... | G16B 20/00 |
| | | | | 702/19 |

FOREIGN PATENT DOCUMENTS

| | | | | |
|---|---|---|---|---|
| CN | 111304303 A | * | 6/2020 | ......... C12Q 1/6858 |
| CN | 112183557 A | | 1/2021 | |
| CN | 113436150 A | | 9/2021 | |
| CN | 114121225 A | | 3/2022 | |
| CN | 114332577 A | | 4/2022 | |
| WO | 2019075251 A2 | | 4/2019 | |

\* cited by examiner

US 12,027,255 B2

SYSTEM FOR PREDICTING MICROSATELLITE INSTABILITY AND CONSTRUCTION METHOD THEREOF, TERMINAL DEVICE AND MEDIUM

CROSS REFERENCE TO RELATED APPLICATIONS

This application is a continuation application of International Application No. PCT/CN2022/114898, filed on Aug. 25, 2022, which claims priority to Chinese Patent Application No. 202210574938.9, filed on May 25, 2022, the entire contents of both of which are incorporated herein by reference.

TECHNICAL FIELD

The present disclosure relates to the field of medical technology, and in particular to a system for predicting microsatellite instability and a construction method thereof, a terminal device and a medium.

BACKGROUND

Microsatellite sequences are short tandem repeating sequence in the human genome, which has poor replication stability and is prone to mismatches, but under normal conditions, it can be recognized by a DNA mismatch repair (MMR) mechanism of a somatic cell of an organism to maintain microsatellite stability (MSS). Moreover, when there is a deficient mismatch repair (dMMR), it can lead to mismatch of the microsatellite sequence, i.e., microsatellite instability (MSI). The MSI occurring at only a single site is defined as microsatellite low instability (MSI-L), and the MSI occurring at more than 2 (inclusive) sites is defined as microsatellite high instability (MSI-H). MSI-H/dMMR is one of important genetic factors of colorectal cancer (CRC), and because this state can cause gene mutation and accumulate mutations continuously, it also has special significance for the treatment and prognosis of the colorectal cancer. The guidelines for the diagnosis and treatment of the colorectal cancer in the United States, Europe, and China all require to make clear whether a patient has MSI-H/dMMR before treatments.

In the prior art, the detection of an MSI-H/dMMR status is obtained by conducting gene detection (MSI-H) or immunohistochemical staining (dMMR) on colonoscopy biopsy specimens or postoperative large pathological specimens, but the colonoscopy method requires increasing the amount of single sample acquisition or even a secondary biopsy, thereby increasing the traumatic property, while the detection of surgical pathological specimens has the defect of timeliness lag. Both the sampling and detection methods increase the time and economic cost and the risk of diagnosis and treatment for the patient.

Therefore, it is necessary to propose a non-invasive and efficient solution to predict the MSI-H/dMMR status.

SUMMARY OF THE INVENTION

A main objective of the present disclosure is to provide a system for predicting microsatellite instability and a construction method thereof, a terminal device and a medium, aiming at realizing non-invasive and efficient prediction of an MSI-H/dMMR status.

In order to achieve the aforementioned objective, the present disclosure provides a system for predicting microsatellite instability comprising:
  an acquisition module for acquiring target image information, pathological specimen information and clinical data information of a user to be predicted;
  a signature generation module for generating a radiomics signature according to the target image information and generating a pathomics signature according to the pathological specimen information, based on a pre-trained MSI-H/dMMR multi-omics signature model;
  a prediction generation module for generating MSI-H/dMMR prediction results according to the radiomics signature, the pathomics signature and the clinical data information, based on the pre-trained MSI-H/dMMR prediction model.

In an embodiment, the system for predicting microsatellite instability further comprises an image preprocessing module, and the image preprocessing module comprises:
  a reading unit for acquiring an enhanced CT image, a magnetic resonance image and a pathological whole slide image (PWSI) of the user to be predicted;
  an image delineation unit for providing the enhanced CT image and the magnetic resonance image to a terminal interface, adopting a region growing image segmentation algorithm to conduct range segmentation, and conducting focus localization based on a revision operation of an operator, so as to obtain a region of interest in the enhanced CT image and a region of interest in the magnetic resonance image;
  a specimen delineation unit for automatically delineating the PWSI by adopting a pre-constructed fully-connected neural network algorithm framework to obtain a region of interest in the PWSI;
  a feature extraction unit for obtaining the target image information and the pathological specimen information by conducting feature extraction on the region of interest in the enhanced CT image, the region of interest in the magnetic resonance image, and the region of interest in the PWSI respectively.

In an embodiment, the feature extraction unit comprises:
  an omics feature extraction unit for conducting omics feature extraction on the region of interest in the enhanced CT image, the region of interest in the magnetic resonance image, and the region of interest in the PWSI respectively, to obtain an omics feature value of the enhanced CT image, an omics feature value of the magnetic resonance image, and an omics feature value of the PWSI;
  a feature output unit for outputting the omics feature value of the enhanced CT image and the omics feature value of the magnetic resonance image as the target image information, and outputting the omics feature value of the PWSI as the pathological specimen information.

In an embodiment, the target image information comprises a first-order feature, shape feature and/or textural feature of a lesion area, the pathological specimen information comprises pixel intensity, morphological features, and/or nuclear texture features of the image.

In an embodiment, the signature generation module comprises:
  an analysis unit for conducting univariate regression analysis on the clinical data information to obtain a relevant clinical risk factor;
  a prediction unit for conducting multivariate regression analysis according to the radiomics signature, the pathomics signature and the relevant clinical risk factor based on the MSI-H/dMMR prediction model, so as to generate the MSI-H/dMMR prediction results.

In an embodiment, the system for predicting microsatellite instability further comprises:

a validation module for verifying the prediction performance of the MSI-H/dMMR prediction model through pre-acquired data of a validation set.

In an embodiment, the acquisition module further comprises a clinical data information unit for collecting the clinical data information, the clinical data information includes gender, age, body mass index, degree of tumor differentiation, serological test results and/or data of a validation set.

Moreover, in order to achieve the objective, the present disclosure further provides a method for constructing a system for predicting microsatellite instability, the method comprises:

constructing an acquisition module for acquiring target image information, pathological specimen information and clinical data information of a user to be predicted;

constructing a signature generation module based on a pre-trained MSI-H/dMMR multi-omics signature model;

constructing a prediction generation module based on a pre-trained MSI-H/dMMR prediction model.

In an embodiment, before the step of constructing a signature generation module based on a pre-trained MSI-H/dMMR multi-omics signature model, the method further comprises:

training to obtain the MSI-H/dMMR multi-omics signature model, specifically including:

acquiring pre-acquired data of sample sets, wherein the data of sample sets includes sample clinical data information, sample image information, sample pathological specimen information, and laboratory detection data of a microsatellite/mismatch repair functional status;

conducting data cleaning on the sample image information and the sample pathological specimen information to obtain valid sample information, and converting a continuous variable in the valid sample information into a dichotomous variable with a median as a margin value to obtain classified sample information;

conducting dimensionality reduction screening on the classified sample information based on the laboratory detection data of the microsatellite/mismatch repair functional status, so as to obtain sample-related information that has a significant association with the MSI-H/dMMR status;

conducting signature vector calculation on the sample-related information to obtain the MSI-H/dMMR multi-omics signature model. In an embodiment, the step of conducting signature vector calculation on the sample-related information to obtain the MSI-H/dMMR multi-omics signature model comprises:

incorporating the sample-related information into a machine learning model to construct an MSI-H/dMMR prediction model, wherein the machine learning model comprises 1D LSTM, logistic regression, naive Bayesian, random forest and/or logistic regression, naive Bayesian, random forest and support vector machine.

In an embodiment, before the step of constructing a prediction generation module based on a pre-trained MSI-H/dMMR prediction model, the method further comprises:

training to obtain the MSI-H/dMMR prediction model, specifically including:

acquiring the sample clinical data information, the sample image information and the sample pathological specimen information in the data of sample sets;

conducting univariate regression analysis on the sample clinical data information to obtain a relevant clinical risk factor of samples;

generating a sample radiomics signature according to the sample image information and generating a sample pathomics signature according to the sample pathological specimen information, based on the MSI-H/dMMR multi-omics signature model;

conducting multivariate regression analysis according to the relevant clinical risk factor of samples, the sample radiomics signature and the sample pathomics signature, to obtain a highly-relevant clinical risk factor of samples that has a significant association with the MSI-H/dMMR status;

training a machine learning model according to the highly-relevant clinical risk factor of samples to obtain the MSI-H/dMMR prediction model.

Moreover, in order to achieve the aforementioned objective, the present disclosure further provides a method of predicting of predicting microsatellite instability, the method comprises:

acquiring target image information, pathological specimen information and clinical data information of a user to be predicted;

generating a radiomics signature according to the target image information, and generating a pathomics signature according to the pathological specimen information, based on a pre-trained MSI-H/dMMR multi-omics signature model having microsatellite high instability and/or deficient mismatch repair;

generating MSI-H/dMMR prediction results according to the radiomics signature, the pathomics signature and the clinical data information, based on the pre-trained MSI-H/dMMR prediction model.

In an embodiment, before the step of acquiring target image information, pathological specimen information and clinical data information of a user to be predicted, the method further comprises:

acquiring an enhanced CT image, a magnetic resonance image and a PWSI of the user to be predicted;

providing the enhanced CT image and the magnetic resonance image to a terminal interface, adopting a region growing image segmentation algorithm to conduct range segmentation, and conducting focus localization based on a revision operation of an operator, so as to obtain a region of interest in the enhanced CT image and a region of interest in the magnetic resonance image;

automatically delineating the PWSI by adopting a pre-constructed fully-connected neural network algorithm framework to obtain a region of interest in the PWSI;

obtaining the target image information and the pathological specimen information by conducting feature extraction on the region of interest in the enhanced CT image, the region of interest in the magnetic resonance image, and the region of interest in the PWSI respectively.

In an embodiment, the step of obtaining the target image information and the pathological specimen information by conducting feature extraction on the region of interest in the enhanced CT image, the region of interest in the magnetic resonance image, and the region of interest in the PWSI respectively, comprises:

conducting omics feature extraction on the region of interest in the enhanced CT image, the region of interest in the magnetic resonance image, and the region of interest in the PWSI respectively, to obtain an omics feature value of the enhanced CT image, an omics feature value of the magnetic resonance image, and an omics feature value of the PWSI;

outputting the omics feature value of the enhanced CT image and the omics feature value of the magnetic resonance image as the target image information, and outputting the omics feature value of the PWSI as the pathological specimen information.

In an embodiment, the step of generating a radiomics signature according to the target image information, and generating a pathomics signature according to the pathological specimen information, based on a pre-trained MSI-H/dMMR multi-omics signature model comprises:

conducting univariate regression analysis on the clinical data information to obtain a relevant clinical risk factor;

conducting multivariate regression analysis according to the radiomics signature, the pathomics signature and the relevant clinical risk factor based on the MSI-H/dMMR prediction model, so as to generate the MSI-H/dMMR prediction results.

Moreover, in order to achieve the aforementioned objective, the present disclosure further provides an apparatus for predicting microsatellite instability, the apparatus comprises:

an acquisition module for acquiring target image information, pathological specimen information and clinical data information of a user to be predicted;

a signature generation module for generating a radiomics signature according to the target image information, and generating a pathomics signature according to the pathological specimen information, based on a pre-trained MSI-H/dMMR multi-omics signature model having microsatellite high instability and/or deficient mismatch repair;

a prediction generation module for generating MSI-H/dMMR prediction results according to the radiomics signature, the pathomics signature and the clinical data information, based on the pre-trained MSI-H/dMMR prediction model.

Moreover, in order to achieve the aforementioned objective, the present disclosure further provides a terminal device comprising a memory, a processor, and a microsatellite instability prediction program stored on the memory and operable on the processor, wherein when executed by the processor, the microsatellite instability prediction program implements the method for constructing a system for predicting microsatellite instability as described above.

Moreover, in order to achieve the aforementioned objective, the present disclosure further provides a computer-readable storage medium, on which a microsatellite instability prediction program is stored, wherein when executed by a processor, the microsatellite instability prediction program implements the method for constructing a system for predicting microsatellite instability as described above.

For the system for predicting microsatellite instability and the construction method thereof, the terminal device and the medium proposed by the embodiments of the present disclosure, by acquiring target image information, pathological specimen information and clinical data information of a user to be predicted by an acquisition module in the system for predicting microsatellite instability; generating a radiomics signature according to the target image information and generating a pathomics signature according to the pathological specimen information, by a signature generation module based on a pre-trained MSI-H/dMMR multi-omics signature model; generating MSI-H/dMMR prediction results according to the radiomics signature, the pathomics signature and the clinical data information, by a prediction generation module based on a pre-trained MSI-H/dMMR prediction model; and classifying the target image information and the pathological specimen information of the user to be predicted to obtain the radiomics signature and the pathomics signature, and in turn generating MSI-H/dMMR prediction results in connection with the clinical data information, non-invasive and efficient prediction of the MSI-H/dMMR status is realized.

Figure 1:
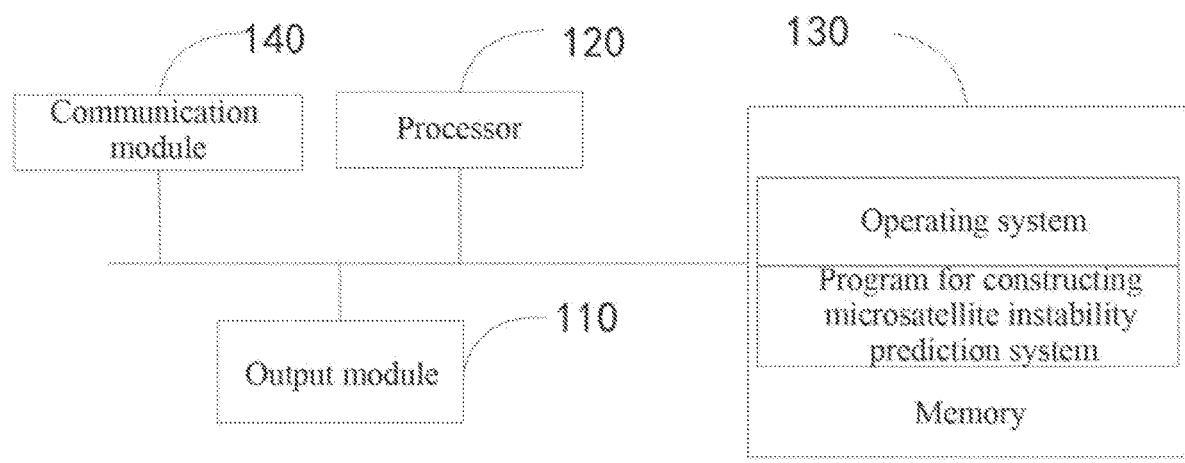
FIG. 1 is a schematic diagram of functional modules of a terminal device to which an apparatus corresponding to a method for constructing a system for predicting microsatellite instability of the present disclosure belongs.

The realization of the objective, functional characteristics and advantages of the present disclosure will be further described in conjunction with embodiments and with reference to the accompanying drawings.

DETAILED DESCRIPTION OF THE EMBODIMENTS

It should be understood that the specific examples described herein are only used for explaining the present invention, but not used for limiting the present invention.

The main solution of the embodiments of the present disclosure is, by: acquiring target image information, pathological specimen information and clinical data information of a user to be predicted by an acquisition module in the system for predicting microsatellite instability; generating a radiomics signature according to the target image information and generating a pathomics signature according to the pathological specimen information, by a signature generation module based on a pre-trained MSI-H/dMMR multi-omics signature model; generating MSI-H/dMMR prediction results according to the radiomics signature, the pathomics signature and the clinical data information, by a prediction generation module based on a pre-trained MSI-H/dMMR prediction model; and classifying the target image information and the pathological specimen information of the user to be predicted to obtain the radiomics signature and the pathomics signature, and in turn generating MSI-H/dMMR prediction results in connection with the clinical data information, non-invasive and efficient prediction of the MSI-H/dMMR status is realized.

Technical terms involved in the embodiments of the present disclosure are set forth in the below:

Microsatellites: Microsatellites;
Mismatch repair: mismatch repair, MMR;
Deficient mismatch repair: deficient mismatch repair, dMMR;
Microsatellite instability: Microsatellite instability, MSI;
Microsatellite low instability: microsatellite low instability, MSI-L;
Microsatellite high instability: microsatellite high instability, MSI-H;
Colorectal cancer: colorectal cancer, CRC;
Pathological whole slide image: pathological whole slide image, PWSI;
Hematoxylin-eosin: hematoxylin-eosin, H&E;
Electron Computed Tomography: Computed Tomography, CT;
T2WI: T2-Weighted Image
DWI: Diffusion-Weighted Image
Magnetic Resonance Imaging: Magnetic Resonance Imaging, MRI (MRI belongs to multi-sequence and multi-modal imaging, and the above two belong to two different sequences of MRI);
Region of interest: region of interest, ROI;
Body mass index: Body Mass Index, BMI;
Long Short-Term Network: Long Short-Term Network, LSTN.

Because the existing MSI-H/dMMR prediction technology only predicts the MSI-H/dMMR status of CRC from one dimension of radiomics or pathomics, it is one-sided and has low accuracy, and it is easy to have false positives or false negatives. Moreover, the prediction based on the pathomics dimension uses a pathological specimen resected in surgery for MSI prediction, which has timeliness lag and cannot provide a patient with MSI information before initial treatment.

The present disclosure provides a solution that combines pre-treatment enhanced CT and multi-modal MRI images with the depth features and omics features of PWSI of colonoscopic biopsy pathological specimens to predict the MSI status of CRC from multiple dimensions of information, which improves the accuracy and comprehensiveness of the prediction. The extraction of image depth features specifically uses CT scan venous phase images, as well as T2WI images of MRI and b=800 s/mm$^2$ images of a DWI sequence. In terms of image segmentation, it is combined with a region growing image segmentation algorithm and a fully-connected neural network algorithm framework respectively to conduct assisted delineation of the ROI in the image, which is also innovative and improved in terms of accuracy and efficiency compared with the previous manual segmentation and extraction based solely on CT or MR tomographic images.

Specifically, referring to FIG. 1, it is a schematic diagram of functional modules of a terminal device to which an apparatus corresponding to a method for constructing a system for predicting microsatellite instability of the present disclosure belongs. The apparatus may be an apparatus independent of the terminal device and capable of conducting prediction of microsatellite instability. It may be carried on the terminal device in a form of hardware or software. The terminal device may be an intelligent mobile terminal with a data processing function, such as a mobile phone, a tablet computer and the like, or may be a fixed terminal device or a server with a data processing function.

In the present embodiments, the terminal device to which the apparatus belongs comprises at least an output module 110, a processor 120, a memory 130 and a communication module 140.

The memory 130 stores an operating system and a program for constructing the system for predicting microsatellite instability therein. The apparatus for constructing the system for predicting microsatellite instability can store the acquired target image information, pathological specimen information and clinical data information of the user to be predicted; the radiomics signature generated according to the target image information and the pathomics signature generated according to the pathological specimen information based on the pre-trained MSI-H/dMMR multi-omics signature model; and the MSI-H/dMMR prediction results generated according to the radiomics signature, the pathomics signature and the clinical data information based on a pre-trained MSI-H/dMMR prediction model, and the like information in the memory 130. The output module 110 may be a display screen, etc. The communication module 140 may comprise a WIFI module, a mobile communication module, and a Bluetooth module, etc., and communication with an external device or server is conducted through the communication module 140.

Wherein, when executed by the processor, the program for constructing the system for predicting microsatellite instability in the memory 130 implements the following steps:
  constructing an acquisition module for acquiring target image information, pathological specimen information and clinical data information of a user to be predicted;
  constructing a signature generation module based on a pre-trained MSI-H/dMMR multi-omics signature model;
  constructing a prediction generation module based on a pre-trained MSI-H/dMMR prediction model.

In an embodiment, when executed by the processor, the microsatellite instability prediction program in the memory 130 further implements the following steps:
  training to obtain the MSI-H/dMMR multi-omics signature model, specifically including:
  acquiring pre-acquired data of sample sets, wherein the data of sample sets comprises sample clinical data information, sample image information, sample pathological specimen information, and MSI detection data;
  conducting data cleaning on the sample image information and the sample pathological specimen information to obtain valid sample information, and converting a continuous variable in the valid sample information into a dichotomous variable with a median as a margin value to obtain classified sample information;
  conducting dimensionality reduction screening on the classified sample information based on the laboratory detection data of the microsatellite/mismatch repair functional status, so as to obtain sample-related information that has a significant association with the MSI-H/dMMR status;
  conducting signature vector calculation on the sample-related information to obtain the MSI-H/dMMR multi-omics signature model.

In an embodiment, when executed by the processor, the microsatellite instability prediction program in the memory 130 further implements the following steps:
  incorporating the sample-related information into a machine learning model to construct an MSI-H/dMMR prediction model, wherein the machine learning model comprises 1D LSTM, logistic regression, naive Bayesian, random forest and/or logistic regression, naive Bayesian, random forest and support vector machine.

In an embodiment, when executed by the processor, the microsatellite instability prediction program in the memory 130 further implements the following steps:

training to obtain the MSI-H/dMMR prediction model, specifically including:
acquiring the sample clinical data information, the sample image information and the sample pathological specimen information in the data of sample sets;
conducting univariate regression analysis on the sample clinical data information to obtain a relevant clinical risk factor of samples;
generating a sample radiomics signature according to the sample image information and generating a sample pathomics signature according to the sample pathological specimen information, based on the MSI-H/dMMR multi-omics signature model;
conducting multivariate regression analysis according to the relevant clinical risk factor of samples, the sample radiomics signature and the sample pathomics signature, to obtain a highly-relevant clinical risk factor of samples that has a significant association with the MSI-H/dMMR status;
training a machine learning model according to the highly-relevant clinical risk factor of samples to obtain the MSI-H/dMMR prediction model.

In an embodiment, when executed by the processor, the microsatellite instability prediction program in the memory 130 further implements the following steps:

acquiring target image information, pathological specimen information and clinical data information of a user to be predicted;
generating a radiomics signature according to the target image information, and generating a pathomics signature according to the pathological specimen information, based on a pre-trained MSI-H/dMMR multi-omics signature model having microsatellite high instability and/or deficient mismatch repair;
generating MSI-H/dMMR prediction results according to the radiomics signature, the pathomics signature and the clinical data information, based on the pre-trained MSI-H/dMMR prediction model.

In an embodiment, when executed by the processor, the microsatellite instability prediction program in the memory 130 further implements the following steps:

acquiring an enhanced CT image, a magnetic resonance image and a PWSI of the user to be predicted;
providing the enhanced CT image and the magnetic resonance image to a terminal interface, adopting a region growing image segmentation algorithm to conduct range segmentation, and conducting focus localization based on a revision operation of an operator, so as to obtain a region of interest in the enhanced CT image and a region of interest in the magnetic resonance image;
automatically delineating the PWSI by adopting a pre-constructed fully-connected neural network algorithm framework to obtain a region of interest in the PWSI;
obtaining the target image information and the pathological specimen information by conducting feature extraction on the region of interest in the enhanced CT image, the region of interest in the magnetic resonance image, and the region of interest in the PWSI respectively.

In an embodiment, when executed by the processor, the microsatellite instability prediction program in the memory 130 further implements the following steps:

conducting omics feature extraction on the region of interest in the enhanced CT image, the region of interest in the magnetic resonance image, and the region of interest in the PWSI respectively, to obtain an omics feature value of the enhanced CT image, an omics feature value of the magnetic resonance image, and an omics feature value of the PWSI;
outputting the omics feature value of the enhanced CT image and the omics feature value of the magnetic resonance image as the target image information, and outputting the omics feature value of the PWSI as the pathological specimen information.

In an embodiment, when executed by the processor, the microsatellite instability prediction program in the memory 130 further implements the following steps:

conducting univariate regression analysis on the clinical data information to obtain a relevant clinical risk factor;
conducting multivariate regression analysis according to the radiomics signature, the pathomics signature and the relevant clinical risk factor based on the MSI-H/dMMR prediction model, so as to generate the MSI-H/dMMR prediction results.

In the present embodiments, through the aforementioned solutions, specifically by constructing an acquisition module for acquiring target image information, pathological specimen information and clinical data information of a user whose MSI status is to be predicted; constructing a signature generation module based on a pre-trained MSI-H/dMMR multi-omics signature model; and constructing a prediction generation module based on a pre-trained MSI-H/dMMR prediction model, a colorectal cancer system for predicting microsatellite instability based on analysis of radiological and pathological depth features is constructed and a construction protocol is provided, so as to predict a MSI-H/dMMR risk value of a CRC patient by comprehensively analyzing the radiological depth/omics features of CT/MRI and pathological depth/omics features of the pathological whole slide image (PWSI) of the patient before treatment in combination with clinical indicators, before treatment.

Figure 2:
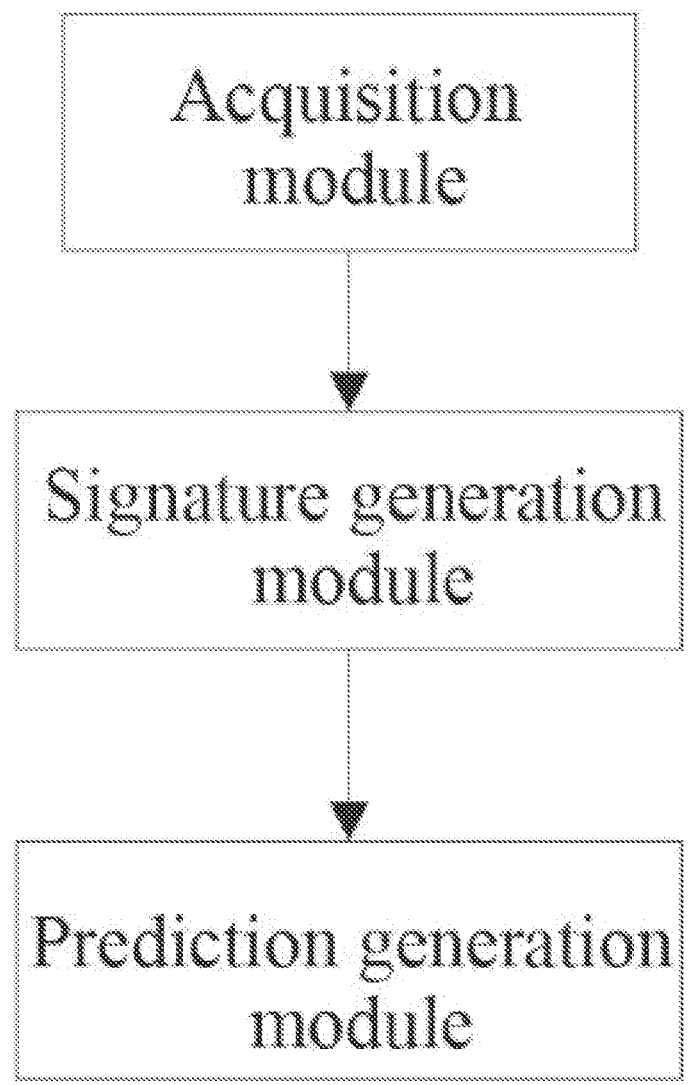
FIG. 2 is a schematic diagram of a basic architecture of the system for predicting microsatellite instability of the present disclosure.

Based on the aforementioned terminal device architecture but not limited to the aforementioned architecture, the present disclosure provides a system for predicting microsatellite instability. Referring to FIG. 2, it is a schematic diagram of a basic architecture of the system for predicting microsatellite instability of the present disclosure. In one embodiment of the system for predicting microsatellite instability of the present disclosure, the system for predicting microsatellite instability comprises:

an acquisition module for acquiring target image information, pathological specimen information and clinical data information of a user to be predicted;
a signature generation module for generating a radiomics signature according to the target image information and generating a pathomics signature according to the pathological specimen information, based on a pre-trained MSI-H/dMMR multi-omics signature model; and
a prediction generation module for generating MSI-H/dMMR prediction results according to the radiomics signature, the pathomics signature and the clinical data information, based on the pre-trained MSI-H/dMMR prediction model.

Before acquiring the target image information, the pathological specimen information and the clinical data information of the user to be predicted by the acquisition module, it is necessary to first retrieve the enhanced CT and multimodal MRI images and PWSIs of colonoscopic biopsy pathological specimens of the user to be predicted before treatment by the image preprocessing module, and then conduct extraction of depth features and omics features to obtain the target image information and the pathological specimen information, including:
- a reading unit for acquiring an enhanced CT image, a magnetic resonance image and a pathological whole slide image (PWSI) of the user to be predicted;
- an image delineation unit for providing the enhanced CT image and the magnetic resonance image to a terminal interface, adopting a region growing image segmentation algorithm to conduct range segmentation, and conducting focus localization based on a revision operation of an operator, so as to obtain a region of interest in the enhanced CT image and a region of interest in the magnetic resonance image;
- a specimen delineation unit for automatically delineating the PWSI by adopting a pre-constructed fully-connected neural network algorithm framework to obtain a region of interest in the PWSI;
- a feature extraction unit for obtaining the target image information and the pathological specimen information by conducting feature extraction on the region of interest in the enhanced CT image, the region of interest in the magnetic resonance image, and the region of interest in the PWSI respectively.

Specifically, the high-resolution T2WI and DWI (b=800 s/mm$^2$) sequence images of the enhanced CT scan (venous phase) and MRI of the adominal and pelvic cavities of the patient with signal intensity and layer thickness (1 mm) standardized by a filter, as pre-stored in the space of an electronic computer system; and PWSIs made by electronic scanning of hematoxylin-eosin (H&E) stained colonoscopic biopsy specimen sections, are retrieved through a path provided by the operator. In turn, a region of interest (ROI) representing a tumor tissue can be delineated based on the CT/MRI image and PWSI of a focus output by an image reading module. For the CT/MRI image, the focus region is delineated by adopting a semi-automatic segmentation manner combined with the region growing image segmentation algorithm and growth points manually delineated by the operator as well as manual revision of the segmentation range after growing. The specific method is illustrated as follows.

The basic principle of the region growing method is first to select a seed point set and merge it with surrounding pixels with similar morphologies (gray levels, textures, etc.), so as to constantly update the seed point set and iteratively merge the surrounding similar pixels until the growth stop condition is met. It mainly includes three main points: (1) selection of an appropriate method and an appropriate number of seeds; (2) determination of the calculation and comparison methods for different pixel point features in a neighborhood (8 or 4 neighborhoods); and (3) determination of conditions for stopping growth.

For the aforementioned three elements, a region growing segmentation method in the present disclosure is set as follows.
- (1) The operator clicks a point representing a tumor tissue with a mouse in a non-necrotic area of a tumor in a tomographic image, and a computer recognizes the point as a seed point and incorporate it into a queue Q.
- (2) The computer uses a gray value as a feature of a pixel point, and a feature comparison manner is to compare it with that of the initial seed (it is considered similar within a range of ±5 gray values); and the computer automatically checks all surrounding pixel points and incorporates a point judged as being similar into Q, with the rest being not processed.
- (3) The growth stop condition is to traverse all the points that meet the requirements in the container. The specific steps are to pop the first element in the queue Q and add it into the set $R_1$. Also, it checks whether Q is empty, and if not, the first element in the current Q is regarded as the seed point, and the step (2) is repeated; otherwise, elements that have not been included in $R_1$ is incorporated into $R_2$, and the growth is stopped.

Correction by the operator: the operator visually judges whether a ROI obtained by natural growth completely covers the tumor region, and whether the range is too large due to over-segmentation. If the aforementioned problems exist, the operator manually corrects the ROI to make it more consistent with the tumor region.

For the PWSI, the region representing the lesion is automatically delineated by adopting the pre-constructed fully-connected neural network algorithm framework. This framework comprises 2 3D U-Net frameworks, and the output of the first framework will be used as an input of the second framework. Each framework contains 4 downsampling regions and 4 upsampling regions, and each layer has two convolutions and one ReLu (rectified linear unit) activation unit. For the generated ROI, a 3D conditional random field and a connected domain analysis algorithm are further adopted to conduct post-processing of a segmentation result to improve the accuracy of segmentation.

In an embodiment, after the region of interest of the CT image, the region of interest in the magnetic resonance image, and the region of interest in the PWSI are delineated, extraction of omics features can be conducted on the ROI of each image by the feature extraction unit, to obtain the corresponding target image information and pathological specimen information, specifically including:
- an omics feature extraction unit for conducting omics feature extraction on the region of interest in the enhanced CT image, the region of interest in the magnetic resonance image, and the region of interest in the PWSI respectively, to obtain an omics feature value of the enhanced CT image, an omics feature value of the magnetic resonance image, and an omics feature value of the PWSI;
- a feature output unit for outputting the omics feature value of the enhanced CT image and the omics feature value of the magnetic resonance image as the target image information, and outputting the omics feature value of the PWSI as the pathological specimen information.

Specifically, radiomics and pathomics feature values are extracted by the omics feature extraction unit based on the ROI of the CT/MRI image and the ROI of the PWSI input by the image preprocessing module. The radiomics feature value includes 1,029 feature values which are used for describing the first-order features (19), shape features (16) and texture features (28 GLCM, 16 GLRLM, 16 GLSZM, 18 GLDM, 411 Wavelets and 505 Logs), respectively. The pathomics feature value includes 820 pathomics feature values, which are used for describing the pixel intensity (175), morphological features (285) and nuclear texture features (360) of the image, respectively. [The omics feature extraction of the CT/MRI and the PWSI is based on Pyradiomics (version 2.1.1, https://github.com/Radiomics/pyradiomics) and a CellProfiler platform (version 2.2.1, https://cellprofiler.org/) respectively].

There is a subjective bias in the radiomics and pathomics analysis method based on a manually delineated ROI. Due to the difference in cognition of the lesion range, there are unstable factors in the process of constructing and using a model. The region growing image segmentation algorithm framework and the fully-connected neural network algorithm framework are embedded in the system constructed by the present disclosure to realize automatic segmentation and identification of the tumor regions in the MRI and PWSI images of the focus, reducing the deviation of the system caused by the instability and inconsistency of the operator.

Moreover, through clinical data acquisition, the clinical data of the patient input by the operator can be acquired, including the gender, age, body mass index (BMI), degree of tumor differentiation (high differentiation=1, medium differentiation=2, and low differentiation=3) and serological test results (CEA, CA-199 serum concentrations). The system will automatically convert the aforementioned continuous variable into a dichotomous variable according to a preset margin value for dichotomy (the margin values for the age, BMI, CEA and CA-199 serum concentrations are respectively: 50 years old, 24 kg/m$^2$, 5 ng/ml and 27 U/ml, the numerical value less than the margin value is defined as class "0", and the numerical value greater than or equal to the margin value is defined as class "1"); and for the classification variable, the degree of tumor differentiation, classes "1", "2" and "3" represent high, medium and low differentiation respectively. In the model construction and validation stages, it still needs to acquire the laboratory detection data of the microsatellite/mismatch repair functional status of the patient, namely MSI-H/dMMR (marked as class "1") or MSI-L/MSS/MMR (marked as class "0") for the construction of the model.

In the process of generating the MSI-H/dMMR prediction results according to the radiomics signature, the pathomics signature and the clinical data information and based on the pre-trained MSI-H/dMMR prediction model, the signature generation module specifically comprises:

an analysis unit for conducting univariate regression analysis on the clinical data information to obtain a relevant clinical risk factor;

a prediction unit for conducting multivariate regression analysis according to the radiomics signature, the pathomics signature and the relevant clinical risk factor based on the MSI-H/dMMR prediction model, so as to generate the MSI-H/dMMR prediction results.

The acquired clinical information of the patient is subjected to univariate regression analysis in the SPSS (Statistics 22; IBM Corp, Armonk, NY) software to screen out a clinical risk factor that has a significant association with the MSI-H status (P<0.05), and combined with the radiomics and pathomics signatures SigCT-MRI and SigPWSI output by the high-frequency MSI prediction model, multivariate regression analysis is conducted to obtain a clinical risk factor that can significantly and independently predict the MSI-H/dMMR status (P<0.05), so as to obtain the MSI-H/dMMR prediction results.

Moreover, the system for predicting microsatellite instability in the present embodiments further comprises a validation module for verifying the prediction performance of the high-frequency MSI prediction model through the pre-acquired data of validation sets.

Specifically, based on the clinical, radiological, and pathological data of 430 CRC patients, the system for predicting colorectal cancer microsatellite instability is constructed and externally verified. Patients are randomly divided into a training group (300 cases) and a validation group (130 cases) according to a ratio of 7:3. The T2WI and DWI (b=800 s/mm$^2$) sequence images of the enhanced CT (venous phase) and MRI that are filtered by a filter and standardized in gray intensity and the PWSIs of the colonoscopic biopsy specimens, of the patients in the training group before treatment, are stored into a given folder. Complete information is input into the clinical data acquisition module, so as to obtain the radiomics and pathomics signature scores and MSI-H/dMMR risk of a specific patient through the pre-trained model. In the present embodiments, by taking the patient to be predicted as a validation case, after all the prediction results are obtained, the actual microsatellite status of the patient is finally input into the system, and the consistency and stability of the model are evaluated according to the deviation between the predicted and actual statuses.

In the present embodiments, by acquiring target image information, pathological specimen information and clinical data information of a user to be predicted by an acquisition module in the system for predicting microsatellite instability; generating a radiomics signature according to the target image information and generating a pathomics signature according to the pathological specimen information, by a signature generation module based on a pre-trained MSI-H/dMMR multi-omics signature model; generating MSI-H/dMMR prediction results according to the radiomics signature, the pathomics signature and the clinical data information, by a prediction generation module based on a pre-trained MSI-H/dMMR prediction model; and classifying the target image information and the pathological specimen information of the user to be predicted to obtain the radiomics signature and the pathomics signature, and in turn generating MSI-H/dMMR prediction results in connection with the clinical data information, non-invasive and efficient prediction of the MSI-H/dMMR is realized.

Figure 3:
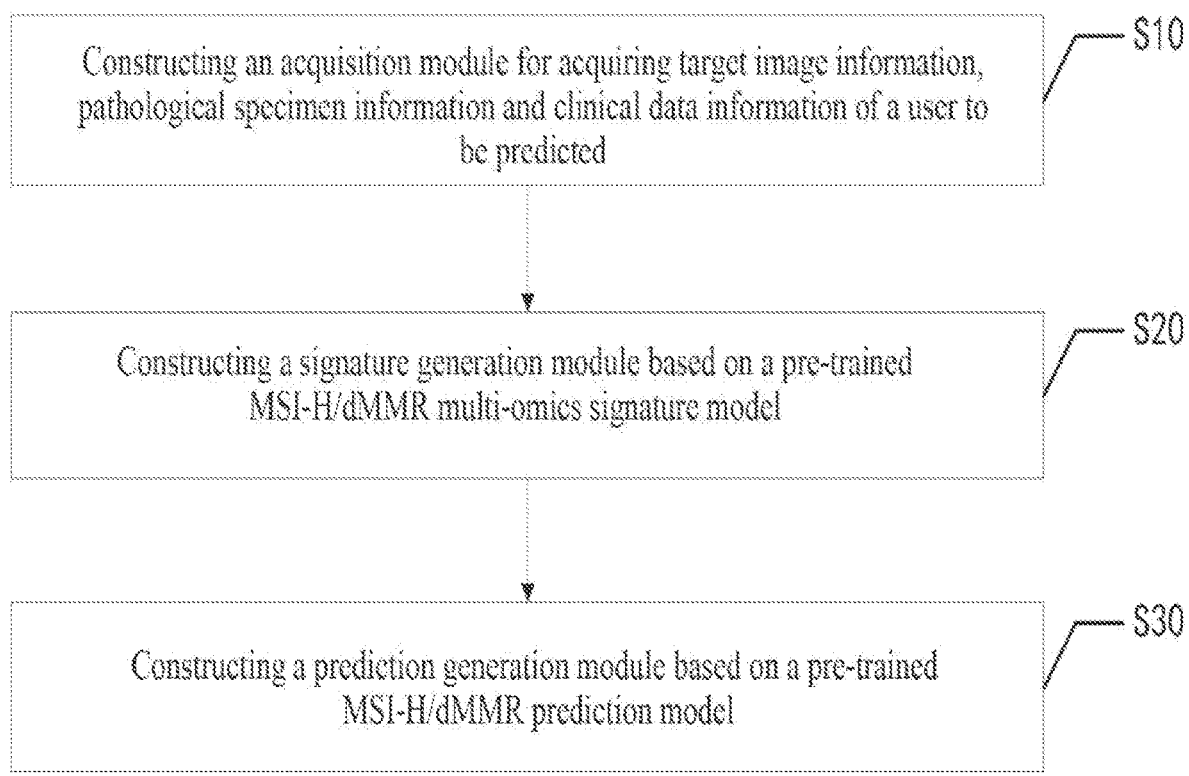
FIG. 3 is a schematic flow chart of an exemplary embodiment of the method for constructing a system for predicting microsatellite instability of the present disclosure.

Referring to FIG. 3, it is a schematic flow chart of an exemplary embodiment of the method for constructing a system for predicting microsatellite instability of the present disclosure. The method for constructing a tumor diagnosis system comprises the following steps.

Step S10. an acquisition module for acquiring target image information, pathological specimen information and clinical data information of a user to be predicted, is constructed.

Specifically, the acquisition module may comprise a clinical data information acquisition module and an information retrieval module. The clinical data of the patient input by the operator is acquired by the clinical data information acquisition module, including the gender, age, body mass index (BMI), degree of tumor differentiation (high differentiation=1, medium differentiation=2, and low differentiation=3) and serological test results (CEA, CA-199 serum concentrations). The system will automatically convert the aforementioned continuous variable into a dichotomous variable according to a preset margin value for dichotomy (the margin values for the age, BMI, CEA and CA-199 serum concentrations are respectively: 50 years old, 24 kg/m$^2$, 5 ng/ml and 27 U/ml, the numerical value less than the margin value is defined as class "0", and the numerical value greater than or equal to the margin value is defined as class "1"); and for the classification variable, the degree of tumor differentiation, classes "1", "2" and "3" represent high, medium and low differentiation respectively. Additionally, in the model construction and validation stages, it still needs to acquire the laboratory detection data of the microsatellite/mismatch repair functional status of the patient (i.e., the MSI-H/dMMR defined as class "1" or the MSI-L/MSS/MMR defined as class "0") for the construction of the model. The information retrieval module can retrieve the target image information and the pathological specimen information obtained through preprocessing and feature extraction.

Step S20. a signature generation module is constructed based on a pre-trained MSI-H/dMMR multi-omics signature model.

Prior to this, it is necessary to obtain the MSI-H/dMMR multi-omics signature model through training. The specific step comprises:
acquiring pre-acquired data of sample sets, wherein the data of sample sets includes sample clinical data information, sample image information, sample pathological specimen information, and laboratory detection data of a microsatellite/mismatch repair functional status;
conducting data cleaning on the sample image information and the sample pathological specimen information to obtain valid sample information, and converting a continuous variable in the valid sample information into a dichotomous variable with a median as a margin value to obtain classified sample information;
conducting dimensionality reduction screening on the classified sample information based on the laboratory detection data of the microsatellite/mismatch repair functional status, so as to obtain sample-related information that has a significant association with a high-frequency MSI status; and
conducting signature vector calculation on the sample-related information to obtain the MSI multi-omics signature model.

Specifically, the sample image information and the sample pathological specimen information in the data of sample sets are the sample image data obtained by delineating the ROI through image preprocessing and feature extraction. According to the sample image information, the sample pathological specimen information, the sample clinical data information and the MSI detection data of the sample, a MSI multi-omics signature model can be constructed to characterize the radiomics and pathomics signatures of MSI-H. This part is mainly divided into three steps, including data cleaning, data dimensionality reduction and signature vector calculation.

More specifically, the data cleaning is mainly responsible for cleaning out invalid data and erroneous data in the multi-omics feature data, and meanwhile transforming a continuous variable into a dichotomous variable with a median as a margin value. The data dimensionality reduction is responsible for conducting significance screening on the multi-omics feature data, wherein data dimensionality reduction is conducted on the radiomics and pathomics feature variables respectively based on the correlation of the dichotomous variable of the omics feature with the MSI-H/dMMR variable, by using a least absolute shrinkage and selection operator (LASSO) formula in R software (version 3.5.1; http://www.Rproject.org), so as to screen out radiomics and pathomics features that that have a significant association with the MSI-H/dMMR status ($p<0.05$). The signature vector calculation is responsible for substituting the features screened out above into different machine learning models to generate multi-omics signatures (SigCT-MRI and SigPWSI) for predicting the MSI-H/dMMR respectively, and conducting analysis and comparison through a receiver operating characteristic (ROC) curve by the system to screen out the radiomics and pathomics signatures (SigCT-MRI and SigPWSI) with the largest area under the curve (AUC). The aforementioned machine learning method includes, but is not limited to 1D LSTM, logistic regression, naive Bayesian, random forest and support vector machine and the like models.

Step S30. a prediction generation module is constructed based on a pre-trained MSI-H/dMMR prediction model.

Prior to this step, it is necessary to obtain the MSI-H/dMMR prediction model through training. The specific step includes:
acquiring the sample clinical data information, the sample image information and the sample pathological specimen information in the data of sample sets;
conducting univariate regression analysis on the sample clinical data information to obtain a relevant clinical risk factor of samples;
generating a sample radiomics signature according to the sample image information and generating a sample pathomics signature according to the sample pathological specimen information, based on the MSI-H/dMMR multi-omics signature model;
conducting multivariate regression analysis according to the relevant clinical risk factor of samples, the sample radiomics signature and the sample pathomics signature, to obtain a highly-relevant clinical risk factor of samples that has a significant association with the MSI-H/dMMR status;
training a machine learning model according to the highly-relevant clinical sample risk factor to obtain the MSI-H/dMMR prediction model.

Specifically, a clinical risk factor that has a significant association with the MSI-H status ($P<0.05$) is screened out based on the patient's clinical information of the sample acquired by the clinical data acquisition module and by using the univariate regression analysis in the SPSS (Statistics 22; IBM Corp, Armonk, NY) software, and combined with the radiomics and pathomics signatures SigCT-MRI and SigPWSI output by the MSI-H/dMMR omics signature construction module, multivariate regression analysis is conducted to obtain a clinical risk factor that can significantly and independently predict the MSI-H/dMMR status ($P<0.05$). The SigCT-MR, the SigPWSI and the clinical risk factor screened out in the multivariate regression analysis are further incorporated into a machine learning model automatically selected by the system to construct a MSI-H/dMMR prediction model. The machine learning model used in this step is the same as the machine learning model used by the signature vector calculation unit in the MSI-H/dMMR omics signature construction module for calculating the omics signature.

In the present embodiments, by constructing an acquisition module for acquiring target image information, pathological specimen information and clinical data information of a user to be predicted; constructing a signature generation module based on a pre-trained MSI-H/dMMR multi-omics signature model; constructing a prediction generation module based on a pre-trained MSI-H/dMMR prediction model, a system for predicting microsatellite instability in colorectal cancer based on analysis of radiological and pathological depth features is constructed and a construction protocol is provided, so as to predict a MSI-H/dMMR risk value of a CRC patient by comprehensively analyzing the radiological depth/omics features of CT/MRI and pathological depth/omics features of the pathological whole slide image (PWSI) of the patient before treatment in combination with clinical indicators, before treatment.

Figure 4:
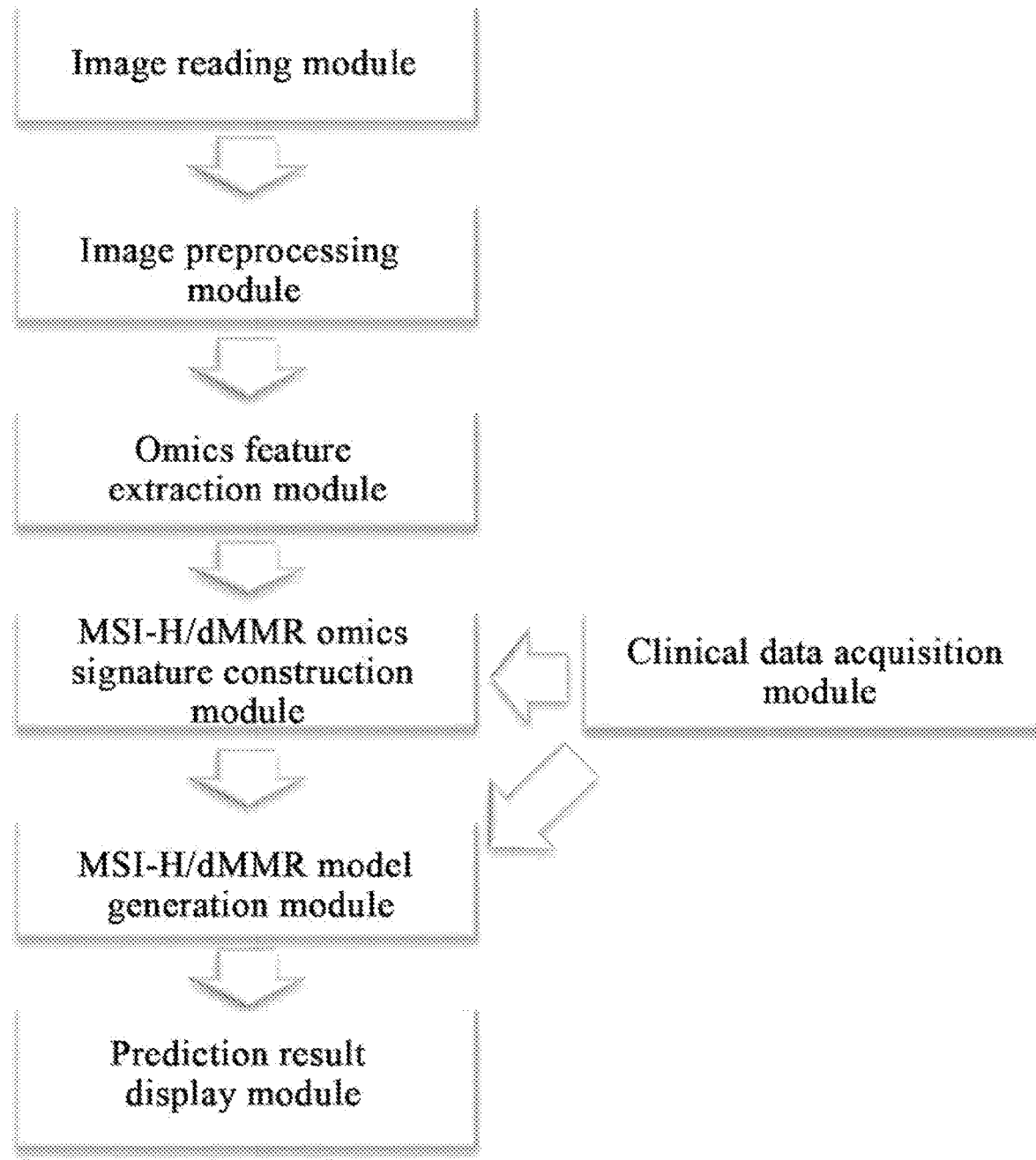
FIG. 4 is a schematic diagram of a second system architecture of the system for predicting microsatellite instability of the present disclosure.

Referring to FIG. 4, it is a schematic diagram of a second system architecture of the system for predicting microsatellite instability of the present disclosure. The system for predicting microsatellite instability in the embodiments of the present disclosure comprises an image reading module, an image preprocessing module, an omics feature extraction module, a clinical data acquisition module, a MSI-H/dMMR omics signature construction module, a MSI-H/dMMR model generation module and a prediction result display module. An output end of the image reading module is connected to an input end of the image preprocessing module. An output end of the image preprocessing module is connected to an input end of the omics feature extraction module. The output ends of the omics feature extraction module and the clinical data acquisition module are connected to an input end of the MSI-H/dMMR omics signature construction module. The output ends of the MSI-H/dMMR omics signature construction module and the clinical data acquisition module are connected to an input end of the MSI-H/dMMR model generation module. An output end of the MSI-H/dMMR model generation module is connected to an input end of the prediction result display module.

In an embodiment, the responsible contents of the image reading module include: the high-resolution T2WI and DWI (b=800 s/mm$^2$) sequence images of the enhanced CT scan (venous phase) and MRI of the adominal and pelvic cavities of the patient with signal intensity and layer thickness (1 mm) standardized by a filter, as pre-stored in the space of an electronic computer system; and PWSIs made by electronic scanning of hematoxylin-eosin (H&E) stained colonoscopic biopsy specimen sections, are retrieved through a path provided by the operator.

In an embodiment, the image preprocessing module is responsible for delineating a region of interest (ROI) representing a tumor tissue based on the CT/MRI image and PWSI of a focus output by the image reading module. For the CT/MRI image, the focus region is delineated by adopting a semi-automatic segmentation manner combined with the region growing image segmentation algorithm and growth points manually delineated by the operator as well as manual revision of the segmentation range after growing. For the PWSI, the region representing the lesion is automatically delineated by adopting the pre-constructed fully-connected neural network algorithm framework. This framework includes 2 3D U-Net frameworks, and the output of the first framework will be used as an input of the second framework. Each framework contains 4 downsampling regions and 4 upsampling regions, and each layer has two convolutions and one ReLu (rectified linear unit) activation unit. For the generated ROI, a 3D conditional random field and a connected domain analysis algorithm are further adopted to conduct post-processing of a segmentation result to improve the accuracy of segmentation.

In an embodiment, the omics feature extraction module is responsible for extracting depth feature values and traditional omics feature values based on the ROI of the CT/MRI image and the ROI of the PWSI input by the image preprocessing module. This module mainly uses a VGG-19 model preliminarily trained by ImageNet large-sample medical image data to extract the depth features from the ROI of the CT/MRI image and the ROI of the PWSI. This model contains 5 stacks, each stack consisting of 2-4 convolutional layers and 1 pooling layer, and finally 3 fully-connected layers. The depth features are mainly extracted by 5 pooling layers and a first fully-connected layer. The omics feature values of the ROI of the CT/MRI image and the ROI of the PWSI are extracted at the same time. The former includes 1,029 feature values for describing the first-order features (19), shape features (16) and texture features (28 GLCM, 16 GLRLM, 16 GLSZM, 18 GLDM, 411 Wavelets and 505 logs) of the focus region respectively. The latter includes 820 pathomics feature values for describing the pixel intensity (175), morphological features (285) and nuclear texture features (360) of the image respectively.

In an embodiment, the clinical data acquisition module is responsible for acquiring the clinical data of the patient input by the operator, including the gender, age, body mass index (BMI), degree of tumor differentiation (high differentiation=1, medium differentiation=2, and low differentiation=3) and serological test results (CEA, CA-199 serum concentrations). The system will automatically convert the aforementioned continuous variable into a dichotomous variable according to a preset margin value for dichotomy (the margin values for the age, BMI, CEA and CA-199 serum concentrations are respectively: 50 years old, 24 kg/m$^2$, 5 ng/ml and 27 U/ml, the numerical value less than the margin value is defined as class "0", and the numerical value greater than or equal to the margin value is defined as class "1"); and for the classification variable, the degree of tumor differentiation, classes "1", "2" and "3" represent high, medium and low differentiation respectively. Additionally, in the model construction and validation stages, it still needs to acquire the laboratory detection data of the microsatellite/mismatch repair functional status of the patient (i.e., the MSI-H/dMMR defined as class "1" or the MSI-L/MSS/MMR defined as class "0").

In an embodiment, the MSI-H/dMMR omics signature construction module is mainly used for screening out and constructing radiomics and pathomics signatures characterizing the MSI-H/dMMR, based on the radiomics feature value input by the radiomics feature extraction module and the microsatellite detection data (modeling stage) input by the clinical data acquisition module. This part is mainly divided into three steps, including data cleaning, data dimensionality reduction and signature vector calculation. The data cleaning is mainly responsible for cleaning out invalid data and erroneous data in the multi-omics feature data, and meanwhile transforming a continuous variable into a dichotomous variable with a median as a margin value. The data dimensionality reduction is responsible for conducting significance screening on the multi-omics feature data, wherein data dimensionality reduction is conducted on the radiomics and pathomics feature variables respectively based on the correlation of the dichotomous variable of the omics feature with the MSI-H/dMMR variable, by using a least absolute shrinkage and selection operator (LASSO) formula in R software (version 3.5.1; http://www.Rproject.org), so as to screen out radiomics and pathomics features that have a significant association with the MSI-H/dMMR status ($p<0.05$). The signature vector calculation is responsible for substituting the features screened out above into different machine learning models to generate multi-omics signatures (SigCT-MRI and SigPWSI) for predicting the MSI-H/dMMR respectively, and conducting analysis and comparison through a receiver operating characteristic (ROC) curve by the system to screen out the radiomics and pathomics signatures (SigCT-MRI and SigPWSI) with the largest area under the curve (AUC). The aforementioned machine learning method includes, but is not limited to 1D LSTM, logistic regression, naive Bayesian, random forest and support vector machine and the like models.

In an embodiment, a clinical risk factor that has a significant association with the MSI-H/dMMR status ($P<0.05$) is screened out by the MSI-H/dMMR model generation module based on the clinical information of the patient acquired by the clinical data acquisition module and by using the univariate regression analysis in the SPSS (Statistics 22; IBM Corp, Armonk, NY) software, and combined with the radiomics and pathomics signatures SigCT-MRI and SigPWSI output by the MSI-H/dMMR omics signature construction module, multivariate regression analysis is conducted to obtain a clinical risk factor that can significantly and independently predict the MSI-H/dMMR status ($P<0.05$). The SigCT-MR, the SigPWSI and the clinical risk factor screened out in the multivariate regression analysis are further incorporated into a machine learning model automatically selected by the system to construct a MSI-H prediction model. The machine learning model used in this step is the same as the machine learning model used by the signature vector calculation unit in the MSI omics signature construction module for calculating the omics signature.

In an embodiment, the prediction result display module will display a structural nomogram of the MSI-H/dMMR prediction model output by the MSI model generation module, as well as the ROC curve representing the prediction performance of the model and the corresponding AUC obtained based on model training or the validation case set. Further, according to the prospective case information (CT/MRI and PWSIs, clinical data) to be predicted as input by the operator subsequently, the system will display the corresponding SigCT-MRI and SigPWSI scores, the model total score and the MSI-H/dMMR risk according to the aforementioned nomogram, so as to achieve prediction of the microsatellite status of the CRC patient before treatment.

Figure 5:
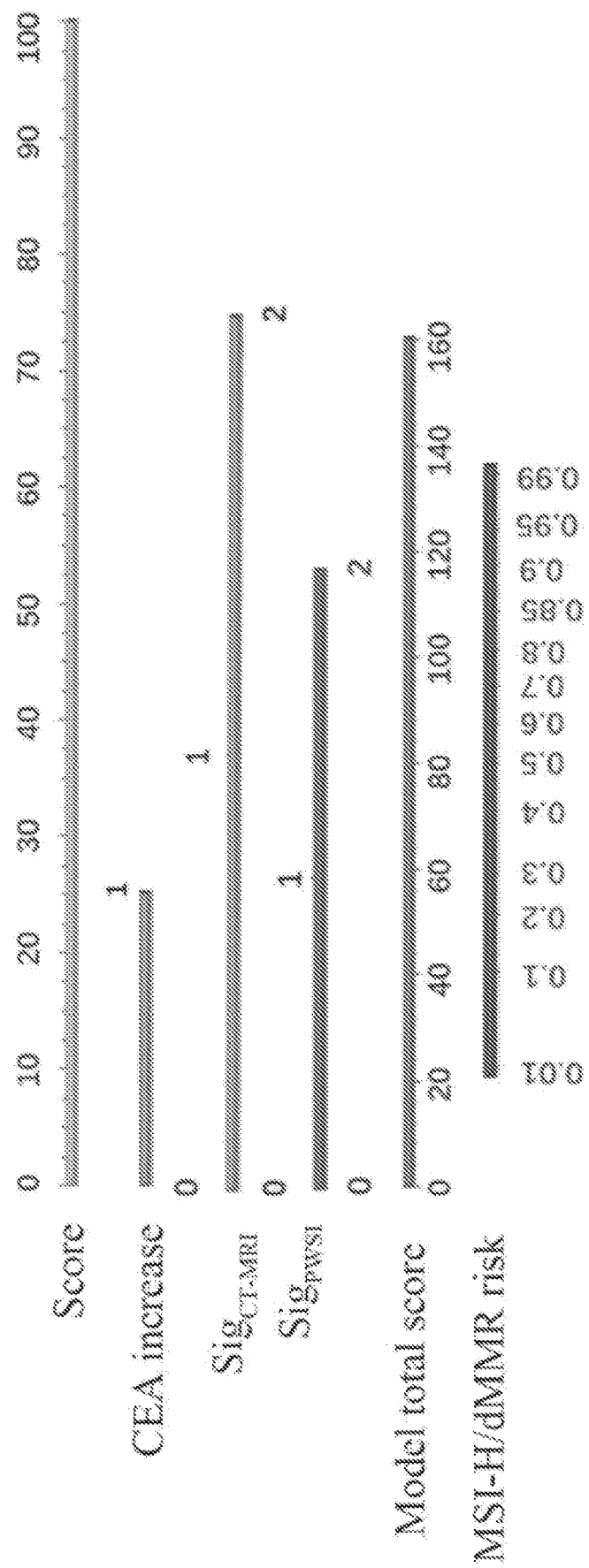
FIG. 5 is an exemplary nomogram displayed by a prediction result display module in an embodiment of the present disclosure.

Referring to FIG. 5, it is an exemplary nomogram displayed by a prediction result display module in an embodiment of the present disclosure. Based on the clinical, radiological, and pathological data of 430 CRC patients, the colorectal cancer system for predicting microsatellite instability is constructed and externally verified. Patients are randomly divided into a training group (300 cases) and a validation group (130 cases) according to a ratio of 7:3. The T2WI and DWI ($b=800$ s/mm$^2$) sequence images of the enhanced CT (venous phase) and MRI that are standardized by a filter and the PWSIs of the colonoscopic biopsy specimens, of the patients in the training group before treatment, are stored into a given folder. Complete information is input into the clinical data acquisition module. Through the aforementioned system model construction process, 5 radiomics features, CT_glcm_JointEnergy, CT_gldm_GrayLevelNonUniformity, CT_gldm_DependenceEntropy, CT_gldm_Dependence Variance and T2WI_glrlm_ShortRunHighGrayLevelEmphasis, are screened out and incorporated into SigPWSI; 4 features, pathomics_feature_374, pathomics_feature_635, pathomics_feature_768 and pathomics_feature_812, are screened out and incorporated into SigPWSI; and the support vector machine model is screened out as the machine learning model for the construction of the omics signature and the final prediction model. The nomogram finally displayed in the prediction result display module after the aforementioned system model construction process, is shown in FIG. 5.

Figure 6:
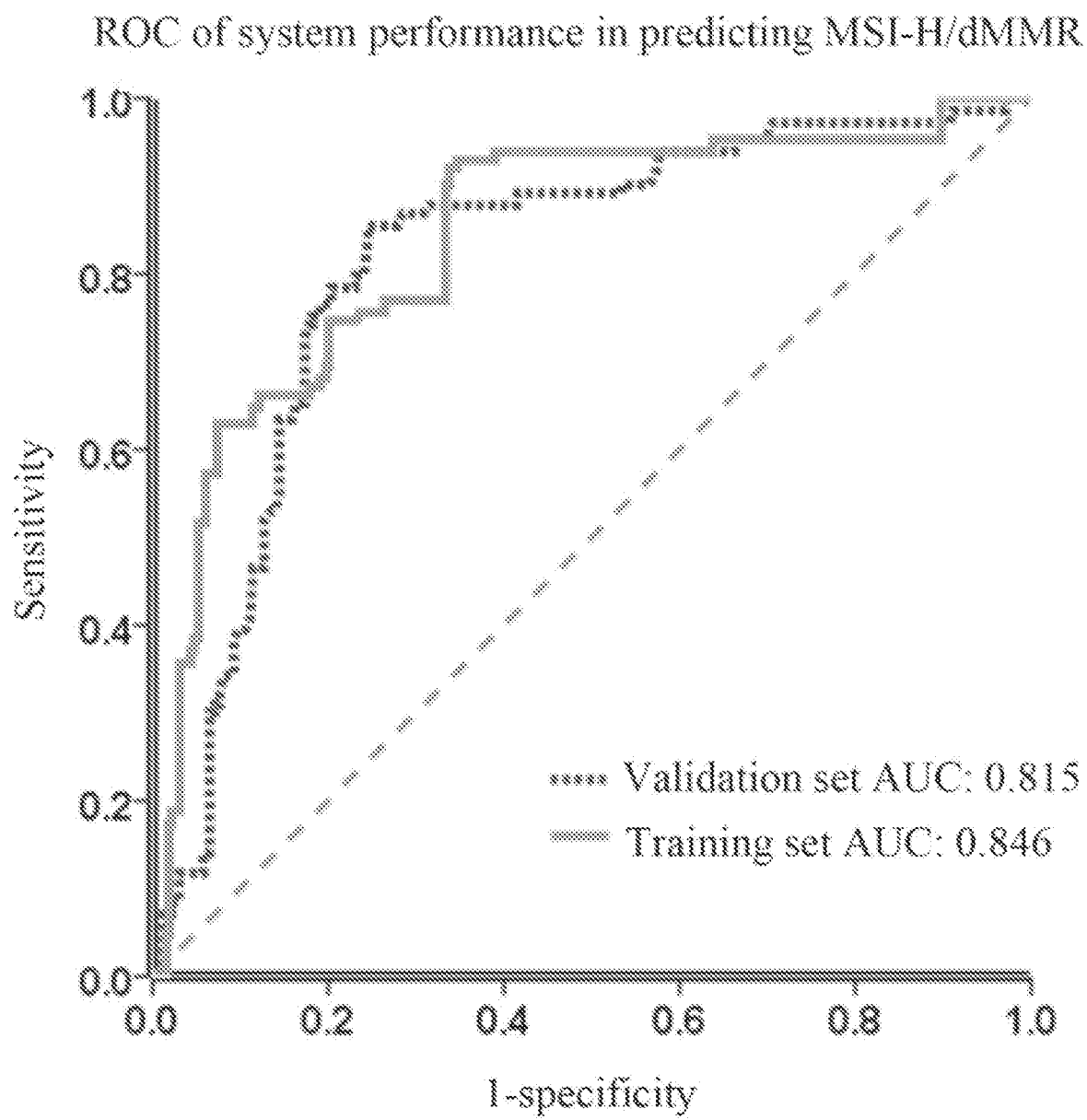
FIG. 6 is a schematic diagram of the prediction performance of a system model on cases in a training set and cases in a validation set in an embodiment of the present disclosure.

Referring to FIG. 6, it is a schematic diagram of the prediction performance of a system model on cases in a training set and cases in a validation set in an embodiment of the present disclosure. After the initial system model construction is completed, the standardized high-resolution T2WI and DWI ($b=800$ s/mm$^2$) sequence images of the enhanced CT (venous phase) and MRI images, the PWSIs and the clinical data (without microsatellite status information) of the patient to be predicted (validation set) are input sequentially, so that the system can calculate and display the radiomics and pathomics signature scores and MSI-H/dMMR risk of a specific patient based on the aforementioned nomogram. In the present embodiments, by taking the patient to be predicted as a validation case, after all the prediction results are obtained, the laboratory detection data of the actual microsatellite/mismatch repair functional status of the patient in the validation set (MSI-H/dMMR marked as class "1" or MSI-L/MSS/MMR marked as class "0") is input into the system, so as to evaluate the consistency and stability of the model according to the deviation between the predicted and actual statuses. As shown in FIG. 6, the predictive performance AUCs of the system model on the cases in the training set and the cases in the validation set reach 0.846 and 0.815, respectively.

In the present embodiments, through the aforementioned schemes, specifically a system for predicting microsatellite instability in colorectal cancer based on the analysis of radiological and pathological depth features is constructed, so as to predict a MSI-H/dMMR risk value of a CRC patient by comprehensively analyzing the radiological depth/omics features of CT/MRI and pathological depth/omics features of the colonoscopic biopsy PWSI of the patient before treatment in combination with clinical indicators, before treatment. Relying on the conventional information and data in the existing clinical diagnosis and treatment process, the microsatellite status of the CRC patient is predicted conveniently and accurately before initial treatment, without increasing the time and economic cost of the patient.

Moreover, the embodiments of the present disclosure further provide a terminal device including a memory, a processor, and a microsatellite instability prediction program stored on the memory and operable on the processor, wherein when executed by the processor, the microsatellite instability prediction program implements the method for constructing a system for predicting microsatellite instability as described above.

Since when executed by the processor, the present microsatellite instability prediction program adopts all the technical solutions of all the aforementioned embodiments, it has at least all the beneficial effects brought by all the technical solutions of all the aforementioned embodiments, the description of which will not be repeated here one by one anymore.

Moreover, the embodiments of the present disclosure further provide a computer-readable storage medium, on which a microsatellite instability prediction program is stored, wherein when executed by a processor, the microsatellite instability prediction program implements the method for constructing a system for predicting microsatellite instability as described above.

Since when executed by the processor, the present microsatellite instability prediction program adopts all the technical solutions of all the aforementioned embodiments, it has at least all the beneficial effects brought by all the technical solutions of all the aforementioned embodiments, the description of which will not be repeated here one by one anymore.

Compared with the prior art, for the system for predicting microsatellite instability and the construction method thereof, the terminal device and the medium proposed by the embodiments of the present disclosure, by acquiring target image information, pathological specimen information and clinical data information of a user to be predicted by an acquisition module in the system for predicting microsatellite instability; generating a radiomics signature according to the target image information and generating a pathomics signature according to the pathological specimen information, by a signature generation module based on a pre-trained MSI-H/dMMR multi-omics signature model; generating MSI-H/dMMR prediction results according to the radiomics signature, the pathomics signature and the clinical data information, by a prediction generation module based on a pre-trained MSI-H/dMMR prediction model; and classifying the target image information and the pathological specimen information of the user to be predicted to obtain the radiomics signature and the pathomics signature, and in turn generating MSI-H/dMMR prediction results in connection with the clinical data information, non-invasive and efficient prediction of the MSI-H/dMMR is realized.

It should be noted that, herein the terms "include", "comprise" or any other variations thereof are intended to cover non-exclusive inclusion, so that a process, method, substance or system including a series of elements includes not only those elements, but also other elements not explicitly listed, or the elements inherent to such process, method, substance or system. Without further limitations, an element defined by the phrase "including a . . . " does not preclude the presence of additional identical elements in the process, method, article or system including that element.

The serial numbers of the aforementioned embodiments of the present application are for description only, and do not represent the advantages and disadvantages of the embodiments.

Through the aforementioned description of embodiments, those skilled in the art can clearly understand that, the methods of the aforementioned embodiments can be implemented by means of software plus a necessary general-purpose hardware platform, of course, can also be implemented by hardware, but in many cases the former is a better embodiment. Based on such understanding, the technical solution of the present application in nature or a part thereof that contributes to the prior art can be embodied in the form of a software product. The computer software product is stored in one of the aforementioned storage media (e.g. ROM/RAM, a magnetic disk, an optical disk), including several instructions to make a terminal device (which may be a mobile phone, a computer, a server, a controlled terminal, or a network device, etc.) execute the method of each embodiment of the present application.

The above are only preferred embodiments, but not intended to limit the patent scope of the present invention. Any equivalent structure or equivalent flow transformation made by using the contents of the specification of the present disclosure and the accompanying drawings, or direct or indirect uses in other related technical fields, are similarly included in the claimed patent scope of the present invention.

What is claimed is:

1. A non-transitory computer-readable storage medium on which a microsatellite instability prediction program is stored, the microsatellite instability prediction program comprising:
   an acquisition module, which when executed by at least one processor, acquires target image information, pathological specimen information and clinical data information of a user to be predicted;
   a signature generation module, which when executed by at least one processor, generates a radiomics signature according to the target image information, and generates a pathomics signature according to the pathological specimen information, based on a pre-trained microsatellite high instability (MSI-H)/deficient mismatch repair (dMMR) multi-omics signature model having microsatellite high instability and/or deficient mismatch repair;
   a prediction generation module, which when executed by at least one processor, generates MSI-H/dMMR prediction results according to the radiomics signature, the pathomics signature and the clinical data information, based on the pre-trained MSI-H/dMMR prediction model;
   the microsatellite instability prediction program further comprises an image preprocessing module, the image preprocessing module comprises a feature extraction unit, the feature extraction unit comprises:
   an omics feature extraction unit, which when executed by at least one processor, conducts omics feature extraction on the region of interest in the enhanced CT image, the region of interest in the magnetic resonance image, and the region of interest in the pathological whole slide image of colonoscopic biopsy pathological specimens respectively, to obtain an omics feature value of the enhanced CT image, an omics feature value of the magnetic resonance image, and an omics feature value of the pathological whole slide image; and
   a feature output unit, which when executed by at least one processor, outputs the omics feature value of the enhanced CT image and the omics feature value of the magnetic resonance image as the target image information, and outputs the omics feature value of the pathological whole slide image as the pathological specimen information,
   wherein before the signature generation module is constructed, the microsatellite instability prediction program is further configured to, when executed by the at least one processor:
   train to obtain the MSI-H/dMMR multi-omics signature model, specifically comprising:
      acquiring pre-acquired data of sample sets, wherein the data of sample sets comprises sample clinical data information, sample image information, sample pathological specimen information, and laboratory detection data of a microsatellite/mismatch repair functional status;
      conducting data cleaning on the sample image information and the sample pathological specimen information to obtain valid sample information, and converting a continuous variable in the valid sample information into a dichotomous variable with a median as a margin value to obtain classified sample information;
      conducting dimensionality reduction screening on the classified sample information based on the laboratory detection data of the microsatellite/mismatch repair functional status, so as to obtain sample-related information that has a significant association with an MSI-H/dMMR status; and
      conducting signature vector calculation on the sample-related information to obtain the MSI-H/dMMR multi-omics signature model.

2. The non-transitory computer-readable storage medium on which a microsatellite instability prediction program is stored according to claim 1, wherein the image preprocessing module further comprises:
   a reading unit for acquiring an enhanced CT image, a magnetic resonance image and a pathological whole slide image of colonoscopic biopsy pathological specimens of the user to be predicted;
   an image delineation unit for providing the enhanced CT image and the magnetic resonance image to a terminal interface, adopting a region growing image segmentation algorithm to conduct range segmentation, and conducting focus localization based on a revision operation of an operator, so as to obtain a region of interest in the enhanced CT image and a region of interest in the magnetic resonance image; and a specimen delineation unit for automatically delineating the pathological whole slide image by adopting a pre-constructed fully-connected neural network algorithm framework to obtain a region of interest in the pathological whole slide image.

3. The non-transitory computer-readable storage medium on which a microsatellite instability prediction program is stored according to claim 1, wherein the signature generation module comprises:

an analysis unit for conducting univariate regression analysis on the clinical data information to obtain a relevant clinical risk factor; and a prediction unit for conducting multivariate regression analysis according to the radiomics signature, the pathomics signature and the relevant clinical risk factor based on the MSI-H/dMMR prediction model, so as to generate the MSI-H/dMMR prediction results.

4. The non-transitory computer-readable storage medium on which a microsatellite instability prediction program is stored according to claim 1, wherein microsatellite instability prediction program further comprises:

a validation module for verifying the prediction performance of the MSI-H/dMMR prediction model through pre-acquired data of a validation set.

5. A method for constructing a system for predicting microsatellite instability, the system comprising executable code stored on a non-transitory recordable storage medium, wherein the system for predicting microsatellite instability is applied in a medical assistance scene, the method of constructing the system for predicting microsatellite instability comprises:

constructing an acquisition module comprising executable code stored on the non-transitory recordable storage medium, the acquisition module configured to, when executed by at least one processor, acquire target image information, pathological specimen information and clinical data information of a user to be predicted;

constructing a signature generation module comprising executable code stored on the non-transitory recordable storage medium, the signature generation module based on a pre-trained MSI-H/dMMR multi-omics signature model;

constructing a prediction generation module comprising executable code stored on the non-transitory recordable storage medium, the prediction generation module based on a pre-trained MSI-H/dMMR prediction model;

the system for predicting microsatellite instability further comprises an image preprocessing module comprising executable code stored on the non-transitory recordable storage medium, the image preprocessing module comprises a feature extraction unit, the feature extraction unit comprises:

an omics feature extraction unit configured to, when executed by the at least one processor, conduct omics feature extraction on the region of interest in the enhanced CT image, the region of interest in the magnetic resonance image, and the region of interest in the pathological whole slide image of colonoscopic biopsy pathological specimens respectively, to obtain an omics feature value of the enhanced CT image, an omics feature value of the magnetic resonance image, and an omics feature value of the pathological whole slide image; and a feature output unit configured to, when executed by at least one processor, output the omics feature value of the enhanced CT image and the omics feature value of the magnetic resonance image as the target image information, and output the omics feature value of the pathological whole slide image as the pathological specimen information, wherein before the step of constructing a signature generation module based on a pre-trained MSI-H/dMMR multi-omics signature model, the method further comprises:

training to obtain the MSI-H/dMMR multi-omics signature model, specifically comprising:

acquiring pre-acquired data of sample sets. wherein the data of sample sets comprises sample clinical data information, sample image information, sample pathological specimen information, and laboratory detection data of a microsatellite/mismatch repair functional status;

conducting data cleaning on the sample image information and the sample pathological specimen information to obtain valid sample information, and converting a continuous variable in the valid sample information into a dichotomous variable with a median as a margin value to obtain classified sample information;

conducting dimensionality reduction screening on the classified sample information based on the laboratory detection data of the microsatellite/mismatch repair functional status, so as to obtain sample-related information that has a significant association with an MSI-H/dMMR status; and conducting signature vector calculation on the sample-related information to obtain the MSI-H/dMMR multi-omics signature model.

6. The method for constructing a system for predicting microsatellite instability according to claim 5, wherein before the step of constructing a prediction generation module based on a pre-trained MSI-H/dMMR prediction model, the method further comprises:

training to obtain the MSI-H/dMMR prediction model, specifically comprising:

acquiring the sample clinical data information, the sample image information and the sample pathological specimen information in the data of sample sets;

conducting univariate regression analysis on the sample clinical data information to obtain a relevant clinical risk factor of samples;

generating a sample radiomics signature according to the sample image information and generating a sample pathomics signature according to the sample pathological specimen information, based on the MSI-H/dMMR multi-omics signature model;

conducting multivariate regression analysis according to the relevant clinical risk factor of samples, the sample radiomics signature and the sample pathomics signature, to obtain a highly-relevant clinical risk factor of samples that has a significant association with the MSI-H/dMMR status; and training a machine learning model according to the highly-relevant clinical risk factor of samples to obtain the MSI-H/dMMR prediction model.

7. A terminal device comprising a memory, a processor, and a microsatellite instability prediction program stored on the memory and operable on the processor, wherein when executed by the processor, the microsatellite instability prediction program implements the method according to claim 5.

* * * * *